United States Patent
Jeon et al.

(10) Patent No.: US 12,070,736 B2
(45) Date of Patent: Aug. 27, 2024

(54) PRE-CONCENTRATOR WITH ALIGNED THREE-DIMENSIONAL POROUS STRUCTURE AND METHOD OF MANUFACTURING THE SAME

(71) Applicant: Korea Advanced Institute of Science and Technology, Daejeon (KR)

(72) Inventors: Seokwoo Jeon, Daejeon (KR); Donghwi Cho, Daejeon (KR); Junyong Park, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 959 days.

(21) Appl. No.: 17/046,042

(22) PCT Filed: Feb. 19, 2019

(86) PCT No.: PCT/KR2019/001943
§ 371 (c)(1),
(2) Date: Oct. 8, 2020

(87) PCT Pub. No.: WO2019/198926
PCT Pub. Date: Oct. 17, 2019

(65) Prior Publication Data
US 2021/0379561 A1    Dec. 9, 2021

(30) Foreign Application Priority Data

Apr. 9, 2018 (KR) .................. 10-2018-0041150

(51) Int. Cl.
*B01D 53/00* (2006.01)
*B01D 53/04* (2006.01)
(Continued)

(52) U.S. Cl.
CPC .... *B01J 20/28095* (2013.01); *B01D 53/0438* (2013.01); *B01J 20/06* (2013.01);
(Continued)

(58) Field of Classification Search
CPC ...... B01J 20/28095; B01J 20/06; B01J 20/08; B01D 53/0438; B01D 2259/40096; G01N 33/0011; G01N 2033/0019; G03F 1/26
(Continued)

(56) References Cited

U.S. PATENT DOCUMENTS 6,527,890 B1 * 3/2003 Briscoe ............... B01L 3/50273
156/89.12
7,273,517 B1 * 9/2007 Lewis ................ G01N 30/6095
95/82

(Continued)

FOREIGN PATENT DOCUMENTS

KR    1020060109477 A  * 10/2006
KR    10-2011-0070509 A    6/2011
(Continued)

OTHER PUBLICATIONS

International Search Report (with English Translation) dated May 28, 2019 for International Application No. PCT/KR2019/001943; 4 Pages.

*Primary Examiner* — T. Bennett McKenzie
(74) *Attorney, Agent, or Firm* — DALY, CROWLEY, MOFFORD & DURKEE, LLP

(57) ABSTRACT

The disclosed pre-concentrator comprises: a base substrate having a trench; a metal layer conformally disposed along the inner surface of the trench; and a three-dimensional porous nanostructure disposed on the metal layer in the trench and having aligned pores connected to each other in three dimensions. The pre-concentrator can improve the concentration performance of a sample and the thermal desorption efficiency of a concentrated sample.

5 Claims, 8 Drawing Sheets

(51) Int. Cl.
  *B01J 20/06*    (2006.01)
  *B01J 20/08*    (2006.01)
  *B01J 20/28*    (2006.01)
  *G01N 33/00*    (2006.01)
  *G03F 1/26*     (2012.01)

(52) U.S. Cl.
  CPC .......... *B01J 20/08* (2013.01); *G01N 33/0011* (2013.01); *B01D 2259/40096* (2013.01); *G01N 33/0019* (2024.05); *G03F 1/26* (2013.01)

(58) Field of Classification Search
  USPC .......................................................... 96/146
  See application file for complete search history.

(56) References Cited

U.S. PATENT DOCUMENTS

| | | | |
|---|---|---|---|
| 9,316,623 B2 | 4/2016 | Seo et al. | |
| 2010/0285412 A1* | 11/2010 | Shew | G03F 7/7035 |
| | | | 430/324 |
| 2013/0260472 A1* | 10/2013 | Holt | C12Q 1/6874 |
| | | | 977/734 |
| 2016/0120442 A1 | 5/2016 | Lim et al. | |
| 2017/0189882 A1 | 7/2017 | Eisele et al. | |

FOREIGN PATENT DOCUMENTS

| | | |
|---|---|---|
| KR | 10-2012-0021647 A | 3/2012 |
| KR | 10-1391730 B1 | 5/2014 |
| KR | 10-2018-0028625 A | 3/2018 |
| WO | WO 2016/008660 A1 | 1/2016 |

* cited by examiner

PRE-CONCENTRATOR WITH ALIGNED THREE-DIMENSIONAL POROUS STRUCTURE AND METHOD OF MANUFACTURING THE SAME

CROSS-REFERENCE TO RELATED APPLICATION

This application is a U.S. National Stage Application of International application No. PCT/KR2019/001943 filed on Feb. 19, 2019. This U.S. non-provisional application claims priorities under 35 USC § 119 from Korean Patent Application No. 10-2018-0041150 filed on Apr. 9, 2018 in the Korean Intellectual Property Office (KIPO), the disclosures of which are hereby incorporated by reference in their entirety.

BACKGROUND

1. Technical Field

The invention relates to a pre-concentrator. More particularly, the invention relates to a pre-concentrator which can be used for detecting volatile organic compounds and a method of manufacturing the pre-concentrator.

2. Description of the Related Art

Recently, needs for detection technologies for detecting various VOCs (volatile organic compounds) are increased. The detection of such volatile organic compounds becomes important in the influence of environment to human body, the detection of diseases, the determination of air conditions, the inspection of explosives, etc. For example, the harmful volatile organic compounds may be evaporated materials in the detection of explosives or poisonous gases existing in air.

The important factor in the detection of the volatile organic compounds can be the concentrations of gas components. However, in many cases, the concentration of gas to be To detect gas components of low concentrations, a pre-concentrator designed for the adsorption/desorption of the gas components can be used. The pre-concentrator can adsorb and concentrate the gas components, and then can discharge the gas components to provide the gas components to a sensor such that the detection limit of the sensor can be enhanced.

In the conventional pre-treatment concentration system, a material for surface coating, which is referred as an adsorbent, can be coated on an inside of a tube. For example, materials including porous polymer such as Tenax® TA, Carboxen®, fumed silica gel, MOFs (Metal-Organic Frameworks) and zeolite can be filled to form a porous structure of large specific surface area which can maximize the efficiency of adsorption/desorption between pores and gas molecules. Then, a gas phase sample can be inserted into the porous structure to be adsorbed to the pores and simultaneously the porous structure can be heated to thermally desorb the gas phase sample to such that the gas phase sample can be concentrated. Therefore, to rapidly and uniformly adsorb/desorb the gas phase sample, there are required the technologies for forming nano structures which can rapidly and uniformly heat the porous structures within short time (technologies related to thermal time constant), can obtain the porous structures of materials having uniform heat transfer (technologies related to thermal conductivity), and can ensure large specific surface areas of porous structures.

Since the conventional pre-treatment concentration system usually includes a random porous structure of micron scale, the system can have basic application limits because of several problems that the desorption efficiency thereof can be reduced by the focusing of heat at some regions in the system, and the movement of the gas phase sample can not be controlled at the time of desorption thereof.

3. PRIOR ART REFERENCES

Patent References (1) PCT International Patent Application No. PCT/EP2015/063293
(2) U.S. Pat. No. 9,316,623

Other References (1) Anal. Chem. 2012, 84, 6336
(2) Lab Chip, 2012, 12, 717
(3) Lab Chip, 2013, 13, 818

SUMMARY

One object of the invention is to provide a pre-concentrator including an arranged three-dimensional porous structure.

Another object of the invention is to provide a method of manufacturing the pre-concentrator.

To accomplish the objects of the invention, there is provided a pre-concentrator comprising a base substrate having a trench, a metal layer conformally disposed on an inside of the trench, and a three-dimensional porous nano structure disposed on the metal layer in the trench, wherein the three-dimensional porous nano structure may have arranged pores three dimensionally connected to each other.

In an example embodiment, the base substrate may include silicon.

In an example embodiment, the trench may include a concentration section, an injection section to which a gas sample is provided, a discharge section for discharging a concentrated gas sample, an injection channel for connecting the concentration section to the injection section, and a discharge channel for connecting the concentration section to the discharge section. Here, the three-dimensional nano structure may be disposed at the concentration section.

In an example embodiment, the pre-concentrator may concentrate a gas sample and provide the gas sample to a separator, and the pre-concentrator and the separator may be disposed on the same substrate.

In an example embodiment, the pre-concentrator may additionally include a cover member coupled to the base substrate to cover the trench and separated from the three-dimensional nano structure.

In an example embodiment, the three-dimensional nano structure may discharge a concentrated gas sample heated using a Joule heat from the metal layer.

To accomplish the objects of the invention, there is provided a method of manufacturing a pre-concentrator, which comprises forming a three-dimensional porous mold in a trench of a base substrate, forming a reverse filled structure by filling pores of the three-dimensional porous mold, and forming a three-dimensional porous nano structure including arranged pores three-dimensionally connected to each other by removing the three-dimensional porous mold.

In an example embodiment, the forming of the three-dimensional porous mold may include forming a metal layer conformally disposed on an inside of the trench, and forming the three-dimensional porous mold on the metal layer.

In an example embodiment, the forming of the three-dimensional porous mold may be performed by an electroplating using the metal as an electrode.

In an example embodiments, the forming of the three-dimensional porous mold may include forming a photosensitive film in the trench; forming an optical medium member on the photosensitive film, disposing a phase mask having a concave and convex structure over the optical medium member, and irradiating a light of a three-dimensional distribution onto the photosensitive film through the phase mask and the optical medium member.

In an example embodiment, the phase mask and the optical medium member may include a substantially same polymer.

In an example embodiment, the phase mask and the optical medium member may include at least one selected from the group consisting of PDMS (polydimetyl siloxane), PUA (polyurethane acrylate) and PEPE (perfluoropolyether).

In an example embodiment, the optical medium member may include glass and at least a portion of the optical medium member may be inserted into the trench.

In an example embodiment, the optical medium member may include a lubricant for matching a refractive index.

In an example embodiment, the three-dimensional nano structure may include at least one selected from the group consisting of cerium oxide ($CeO_2$), aluminum oxide ($Al_2O_3$), titanium oxide ($TiO_2$), zirconium oxide ($ZrO_2$), zinc oxide (ZnO) and titanium nitride (TiN).

In an example embodiment, the three-dimensional nano structure may include at least one selected from the group consisting of gold, silver, platinum, palladium, ruthenium, rhodium, iridium, vanadium, nickel, cobalt, copper, tungsten, molybdenum, manganese, aluminum and iron.

In example embodiments, the forming of the three-dimensional porous mold may include forming a photosensitive film in the trench, contacting a phase mask having a concave and convex structure with a lower face of the base substrate where the trench is not formed; and irradiating a light of a three-dimensional distribution onto the photosensitive film through the phase mask and the base substrate.

According to example embodiments of the invention, the pre-concentrator may be used in the concentration of the gas sample. The three-dimensional nano structure may have a three-dimensionally connected network structure so that the three-dimensional nano structure may ensure uniform and rapid heat transfer and small weight with high porosity. Therefore, the three-dimensional nano structure may heat the gas sample with low energy and uniformly hear the sample within short time, and then may discharge the gas sample of high density within short time. As a result, the pre-concentrator may have improved concentration performance. Further, the three-dimensional nano structure may minimize back-pressure thereof. Moreover, the three-dimensional nano structure may be rapidly heated by a metal heating member and the metal heating member may be used as a plating electrode for forming the three-dimensional nano structure.

DETAILED DESCRIPTION OF THE EMBODIMENTS

Figure 1:
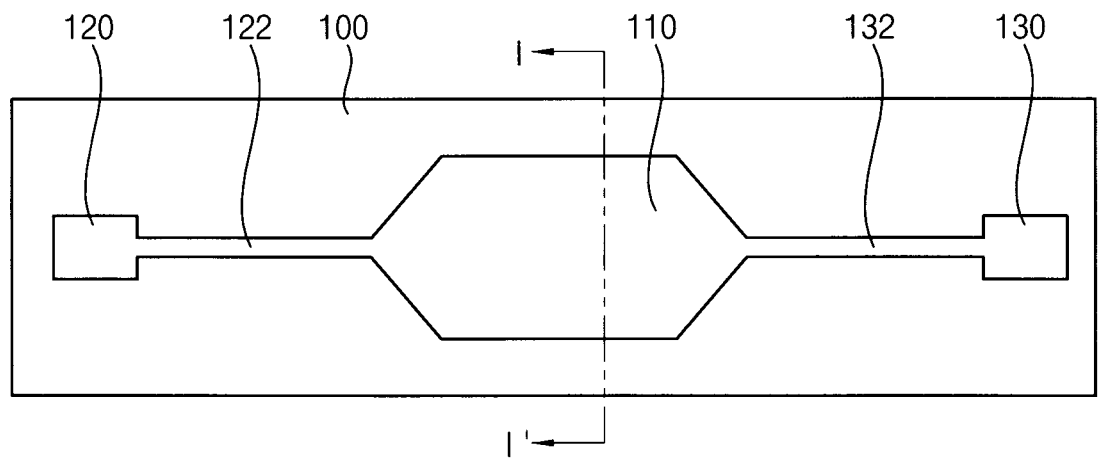
FIG. 1 is a plan view illustrating a pre-concentrator in accordance with an example embodiment of the invention.

Various embodiments will be described more fully hereinafter with reference to the accompanying drawings, in which some embodiments are shown. The invention may, however, be embodied in many different forms and should not be construed as limited to the embodiments set forth herein. Rather, these embodiments are provided so that this description will be thorough and complete, and will fully convey the scope of the invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a," "an" and "the" are intended to include a plurality of forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments of the invention will be described with reference to the accompanying drawings. In the drawings, the same reference numerals are used for the same elements and redundant explanations for the same elements will be omitted.

Figure 2:
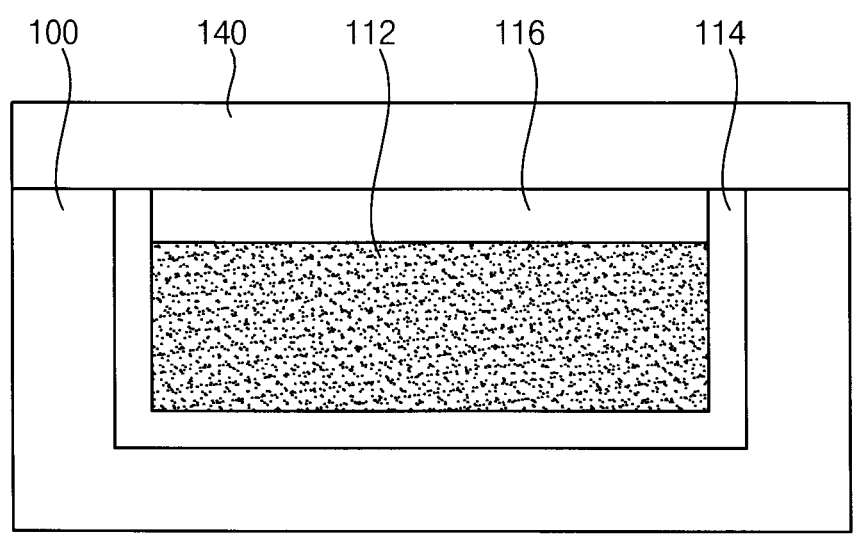
FIG. 2 is a cross sectional view taken along a line of I-I' in FIG. 1.

FIG. 1 is a plan view illustrating a pre-concentrator in accordance with an example embodiment of the invention. FIG. 2 a cross sectional view taken a long a line of I-I' in FIG. 1.

Referring to FIGS. 1 and 2, the pre-concentrator according to the invention may include a base substrate 100. A trench may be formed on the base substrate 100. The trench may include a concentration section 110, an injection section 120 and a discharge section 130. Additionally, the trench may include an injection channel 122 for connecting the concentration section 110 to the injection section 120 and a discharge channel 132 for connecting the concentration section 110 to the discharge section 130.

In example embodiments, the base substrate 100 may include a semiconductor material such as silicon. In some example embodiments, the base substrate 100 may include a transparent material such as glass, quartz, sapphire, PMMA (polymethyl methacrylate), PET (polyethyleneterephthalate), PC (polycarbonate), PI (polyimide), PA (polyamide), PP (polypropylene), etc.

A three-dimensional nano structure 112 may be disposed in the concentration section 110. The three-dimensional nano structure 112 may have arranged pores three-dimensionally connected to each other. The three-dimensional nano structure 112 may include various materials such as metal, ceramic, semiconductor, organic compounds, etc. For example, the three-dimensional nano structure 112 may include cerium oxide ($CeO_2$), aluminum oxide ($Al_2O_3$), titanium oxide ($TiO_2$), zirconium oxide ($ZrO_2$), zinc oxide (ZnO), titanium nitride (TiN), or combinations thereof. In another example embodiment, the three-dimensional nano structure 112 may include gold, silver, platinum, palladium, ruthenium, rhodium, iridium, vanadium, nickel, cobalt, copper, tungsten, molybdenum, manganese, aluminum, iron, or combinations thereof. The materials for the three-dimensional nano structure 112 of the invention may not be limited to the above materials, and thus various materials may be used for the three-dimensional nano structure 112 depending on types of substances to be detected.

The three-dimensional nano structure 112 may be enclosed by a metal layer 114. For example, the metal layer 114 may be disposed on an inside of the trench and the three-dimensional nano structure 112 may be formed on the metal layer 114.

The metal layer 114 may serve as a heating member. To discharge a sample gas absorbed and concentrated by the three-dimensional nano structure 112, the three-dimensional nano structure 112 may be heated through the metal layer 114. For example, the metal layer 114 may generate Joule heat by applying current thereto.

Additionally, the metal layer 114 may be used as a plating electrode when the three-dimensional nano structure 112 is formed an electroplating process.

In an example embodiment, the pre-concentrator may be combined with the base substrate 100. The pre-concentrator may include a cover member 140. The cover member 140 and the three-dimensional nano structure 112 may be separated such that a gap 116 may be formed therebetween. The gap 116 may be used as a path for a gas which may be provided into the pre-concentrator. Additionally, the gap 116 may be formed to provide a manufacturing margin for a distributor or a sensor, which may be integrally formed with the pre-concentrator.

In an example embodiment, the three-dimensional nano structure 112 may have a three-dimensional network configuration in which nano-scaled pores may be three-dimensionally connected to each other and may be arranged with a predetermined periodicity. That is, the three-dimensional nano structure 112 may have a wholly opened structure in which substantial all of the pores may be interconnected therein.

Accordingly, efficient mass transfer may be accomplished in the above structure and the surface area of the structure may be maximized such that the pre-concentrator may have increased concentration performance.

Additionally, the three-dimensional nano structure 112 may not include a plurality of particles, but may have the network configuration in which the pores are interconnected so that the three-dimensional nano structure 112 may have uniform and rapid heat transfer coefficient and may have small weight due to high porosity thereof. Therefore, the pre-concentrator may be heated with low energy and may be uniformly heated within short time to thereby discharge a gas sample with high density and short time. As a result, the pre-concentrator may ensure improved concentration performance.

Further, the three-dimensional nano structure 112 may minimize the back-pressure of the pre-concentrator.

FIGS. 3 to 8 are cross sectional views illustrating a method of manufacturing a pre-concentrator in accordance with example embodiments of the invention. FIG. 9 is a perspective view illustrating a step of forming a three-dimensional nano structure in accordance with example embodiments of the invention.

Figure 3:
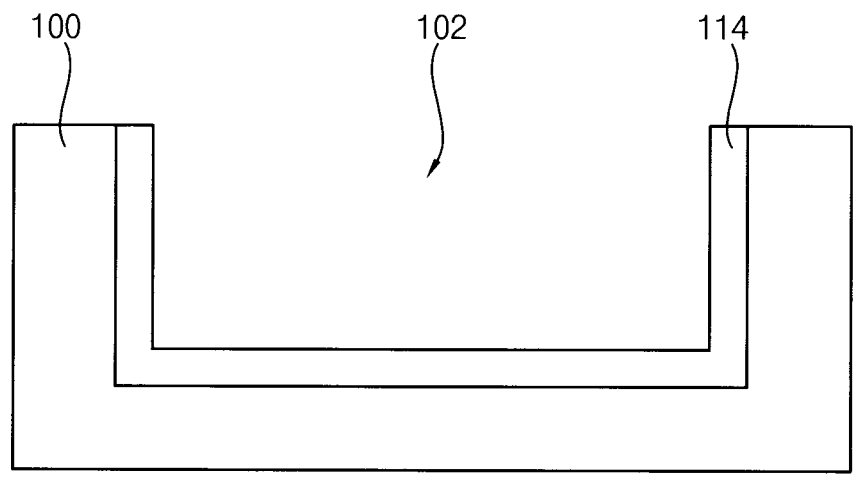
FIGS. 3 to 8 are cross sectional views illustrating a method of manufacturing a pre-concentrator in accordance with an example embodiment of the invention.

Referring to FIG. 3, a metal layer 114 may be formed in a trench 102 of a base substrate 100. The metal layer 114 may be conformally formed along an inner wall of the trench 102.

Various metals may be used for the metal layer 114 without any limitation. For example, the metal layer 114 may include copper (Cu), aluminum (Al), silver (Ag), nickel (Ni), gold (Au), cobalt (Co), titanium (Ti), chrome (Cr), indium tin oxide (ITO), etc. The metal layer 114 may be formed by various known processes for forming metal layers. For example, a metal layer may be formed in and on the trench 102 of the base substrate 100 by a sputtering process, and then a polishing process may be performed to expose an upper face of the base substrate 100 such that the metal layer 104 may be formed in the trench 102.

Figure 4:
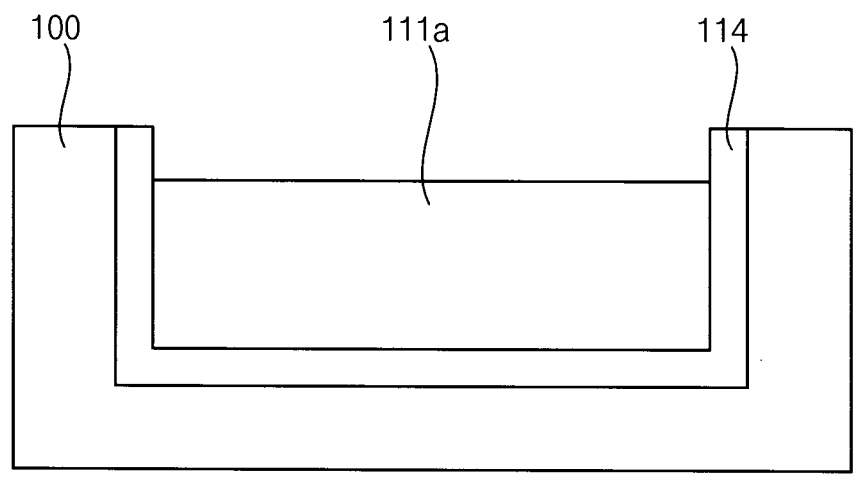

Referring to FIG. 4, a photosensitive film 111a may be formed in the trench 102. The photosensitive film 111a may be formed by treating a photosensitive composition using a soft baking process, for example, at a temperature range of about 90° C. to about 100° C. after the photosensitive composition is provided in the trench 102.

The photosensitive composition for the photosensitive film 111a may include epoxy based negative-tone photoresist or DNQ based positive-tone photoresist. In an example embodiment, the photosensitive composition may include an organic or inorganic hybrid material, hydrogel, phenolic resin, etc.

In an example embodiment, the photosensitive film 111a may have a thickness smaller than a depth of the trench 102. Thus, an upper face of the photosensitive film 111a may be substantially lower than an upper face of the base substrate 100.

Figure 5:
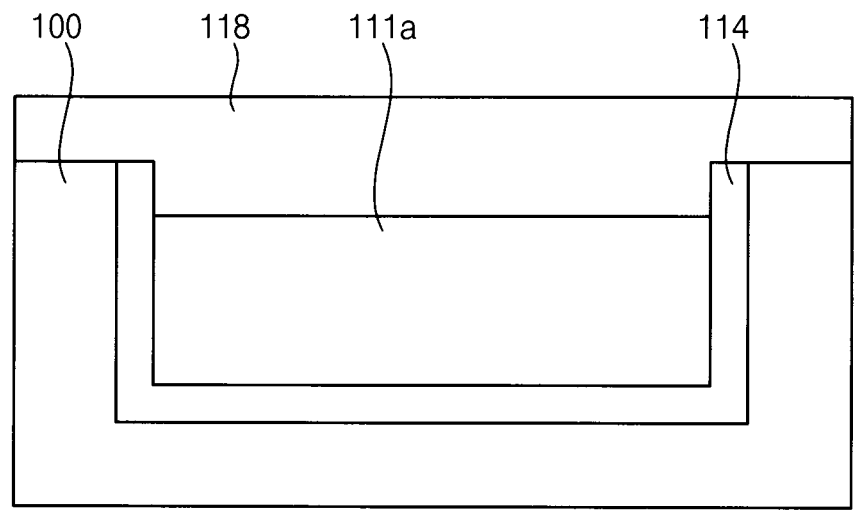

Referring to FIG. 5, an optical medium member 118 may be formed on the photosensitive film 111a. The optical medium member 118 may effetely transmit a light to the photosensitive film 111a in a successive near-field nano patterning (PnP) process.

As described above, the upper face of the photosensitive film 111a may be lower than the upper face of the base substrate 100. In this case, a gap may be generated between the photosensitive film 111a and a phase mask even though the phase mask is tightly attached to the base substrate 100. If the near-field nano patterning process is carried out in this state, the patterning process may not be performed on an underlying structure below the photosensitive film 111a.

In an example embodiment of the invention, the optical medium member 118 may include a polymer film including macromolecules. Preferably, the optical medium member 118 may include the same macromolecules as those of the phase mask and may include, for example, PDMS (polydimethylsiloxane), PUA (polyurethane acrylate), PFPE (perfluoropolyether), etc. To obtain the optical medium member 118, a polymer composition or a monomer composition may be coated on the photosensitive film 111a, and then may be dried or cured.

In another example embodiment, the optical medium member 118 may include glass. For example, the optical medium member 118 may include a protrusion corresponding to the trench 102, and the protrusion may be aligned to be inserted into the trench 102. Sine glass has a refractive index (greater than 1.46) greater than that of PDMS (a refractive index: 1.45), the optical medium member 118 may have a refractive index more similar to that of the photosensitive film 111a (a refractive index: for example, 1.65 to 1.7, and 1.67 for Su-8 (trade name)). Therefore, the glass may be more effectively transmit a three-dimensionally distributed light to the photosensitive film 111a rather than PDMS. Preferably, the glass for the optical medium member 118 may include soda lime glass having a refractive index greater than that of general glass.

In another example embodiment, the optical medium member 118 may include a lubricant for matching a refractive index. The lubricant for matching a refractive index may be a liquid phased mixture and may be provided to fill the trench 102.

Figure 6:
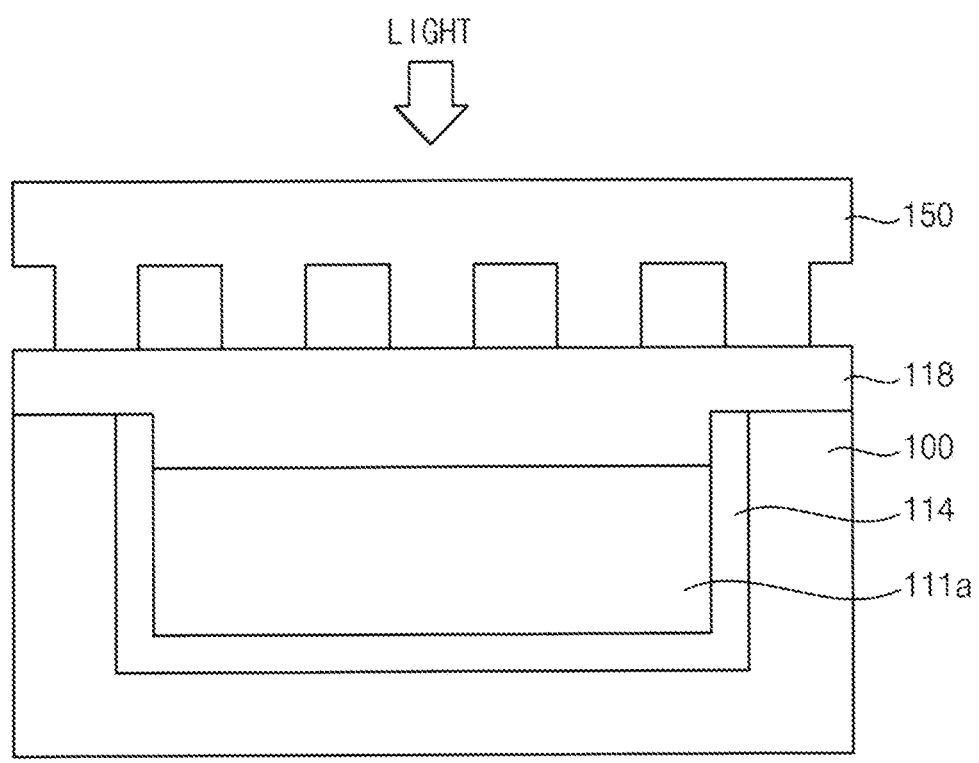
Figure 7:
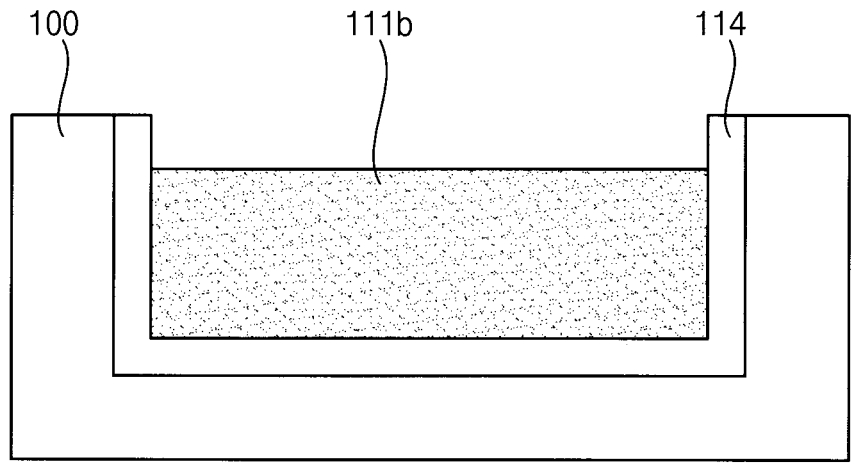

Referring to FIG. 6 and FIG. 7, the near-field nano patterning process may be performed to form a three-dimensional porous mold 111b. Particularly, a phase mask 150 may contact an upper face of the optical medium member 118, and then the three-dimensionally distributed light may be irradiated onto the photosensitive film 111a through the phase mask 150 and the optical medium member 118.

In the near-field nano patterning (PnP) process, the photosensitive film 111a may be patterned, for example, by utilizing the periodic three-dimensional distribution of light generated from the interference of light passing through a phase mask including an elastomer material. For example, when the flexible elastomer based phase mask 150 having a concave and convex grid structure on a surface thereof may contact the optical medium member 118, the phase mask 150 may be adhered (for example, conformally contacted) to the optical medium member 118 by itself because of a Van der Waals force.

If a laser having a range of wavelengths similar to a grating period of the phase mask 150 is irradiated onto the surface of the phase mask 150, the three-dimensional distribution of light may be accomplished by Talbot effect. When the negative-tone photoresist is used, cross linking may be generated at portions of the photoresist on which light is strongly irradiated due to the constructive interference of light, whereas other portions of the photoresist on which light is weakly irradiated may be dissolved and removed in a developing process because of the insufficient exposure dose of light. After a final drying process, a porous polymer material may be obtained, which may contain periodical three-dimensional structures of several hundreds nanometers (nm) to several micrometers (μm) depending on a wavelength of a laser and a design of a phase mask.

In some example embodiments, the size and periodicity of the pores in the three-dimensional porous mold 111b nay be adjusted by controlling the pattern period of the phase mask 150 and the wavelength of incident light in the PnP process.

The PnP process is disclosed in J. Phys. Chem. B 2007, 111, 12945-12958; Proc. Natl. Acad. Sci. U.S.A. 2004, 101, 12428; AdV. Mater. 2004, 16, 1369 and Korean Patent Publication No. 2006-0109477 (published on Oct. 20, 2006), disclosures of which are incorporated herein by the references.

In some example embodiments, the phase mask used in the PnP process may include a material such as PDMS (polydimetyl siloxane), PUA (polyurethane acrylate), PEPE (perfluoropolyether), etc.

For example, a photoresist film may be coated on a silicon wafer by a spin coating process, and then a silicon master including a photoresist pattern may be obtained by an exposure process and a developing process. A surface of the silicon master may be treated, for example, by using a vapor of perfluorinated trichlorosilane. After a PDMS layer may be coated on the silicon master, and then the silicon master having the PDMS layer thereon may be cured and separated to thereby obtain an elastomer phase mask.

In some example embodiments, when the photosensitive film 111a includes the negative-tone photoresist, an unexposed portion of the photosensitive film 111a may remains while an exposed portion thereof may be removed. Thus, the three-dimensional porous mold 111b including three-dimensional nano pores may be formed. Examples of a developing solution may include, for example, PGME (propylene glycol monomethyl ether acetate). The optical medium member 118 may be removed by a physical process.

The three-dimensional porous mold 111b may have a three-dimensional network structure in which nano-scaled pores in a range of about 1 nm to about 2,000 nm are connected in a three dimensions and arranged with a predetermined periodicity.

As described above, although the PnP process is exemplary explained, the invention may not be limited to the above description, and a three-dimensional porous mold may also be formed by a layer-by-layer self assembly process, a particle self assembly process, a multiple beam interference lithography process, etc.

Figure 8:
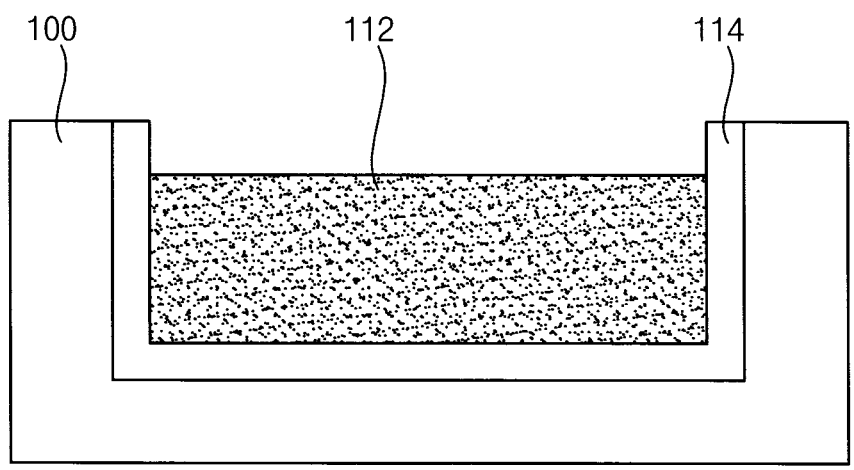
Figure 9:
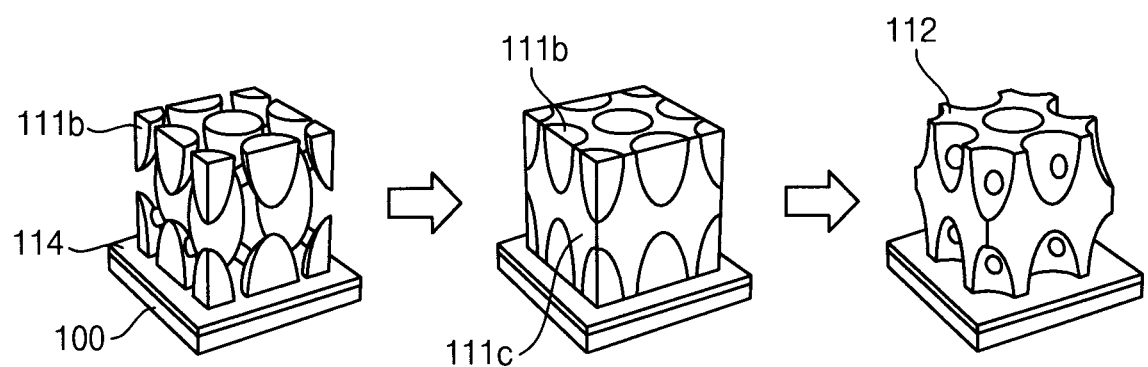
FIG. 9 is a perspective view illustrating a step of forming a three-dimensional nano structure in accordance with an example embodiment of the invention.

Referring to FIG. 8 and FIG. 9, using the three-dimensional porous mold 111b, the three-dimensional nano structure 112 may be obtained.

In particular, at least a portion of the three-dimensional porous mold 111b may be filled to form a reverse filled structure 111c. Then, the three-dimensional porous mold 111b may be removed such that the three-dimensional nano structure 112 corresponding to the filled structure 111c may be obtained.

For example, the three-dimensional nano structure 112 may be formed by a chemical vapor deposition process, an atomic layer deposition process, an electroplating process, an electroless plating process, a liquid metal infiltration process, etc.

In an example embodiment, the three-dimensional nano structure 112 may be obtained by the electroplating process. In an example embodiment, the three-dimensional porous mold 111b may be enclosed by the metal layer 114. Therefore, the electroplating process may be uniformly and rapidly performed using the metal layer 114 as a plating electrode.

The three-dimensional nano structure 112 may be removed by a plasma etching process, a wet etching process, etc.

In example embodiments, an activated reactive material may be coated on a surface of the three-dimensional nano structure 112 so as to improve the detection effect of the three-dimensional nano structure 112. The activated reactive material may be reacted with the substance to be detected on the surface of the three-dimensional nano structure 112.

The activated reactive material may include various materials as the following chemical formulas in accordance with the types of the substances to be detected. For example, when the substance to be detected is a material (e.g., cotain, heroin, morphine, methamphetamine, ecstasy, ketamine, etc.) containing a functional group of a H-bond acceptor (represented by dotted lines) as represented by the following chemical formula 1-1, a material containing a functional group of a H-bond donor as represented by the following chemical formula 1-2 may be used as the activated reactive material.

[Chemical formula 1-1]

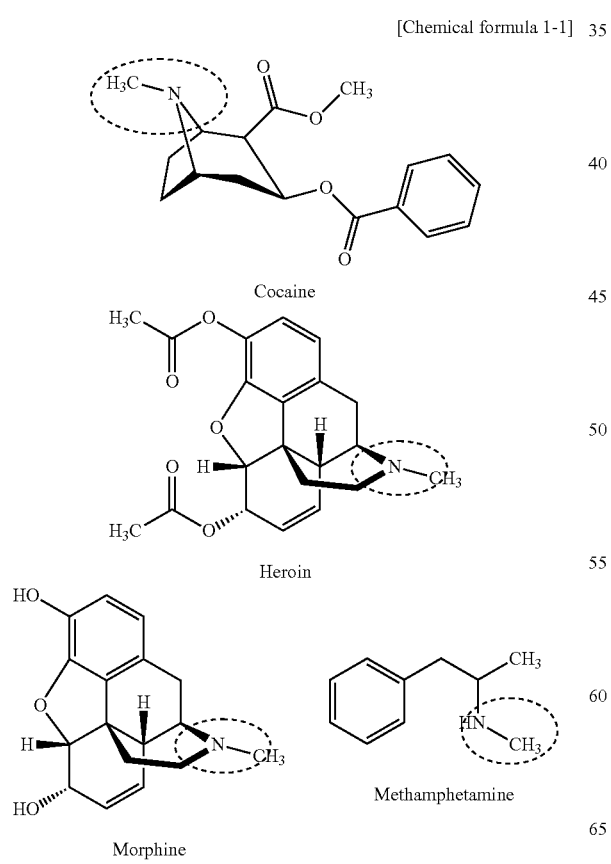

[Chemical formula 1-2]

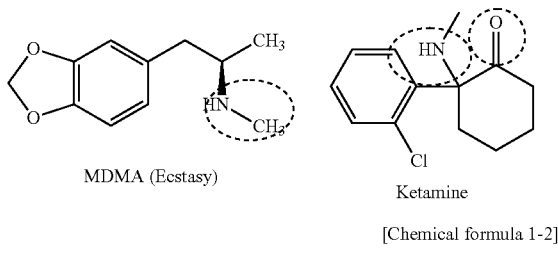

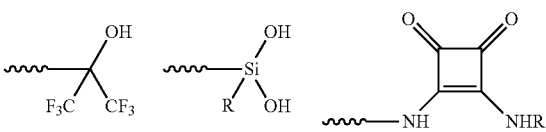

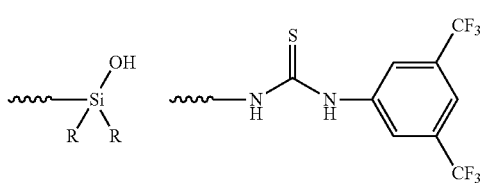

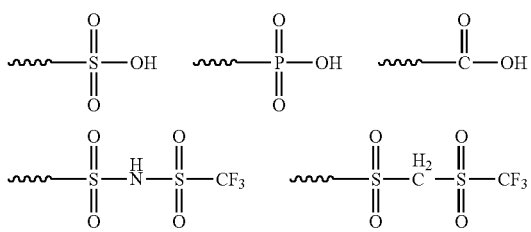

Further, when the substance to be detected is a material (e.g., LSD, marihuana, morphine, etc.) containing a functional group of a charge-transfer donor (represented by dotted lines) as represented by the following chemical formula 2-1, a material containing a functional group of a charge-transfer acceptor as represented by the following chemical formula 2-2 may be used as the activated reactive material.

[Chemical formula 2-1]

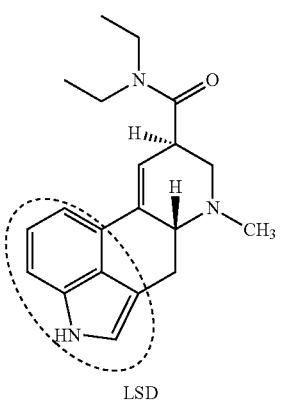

-continued

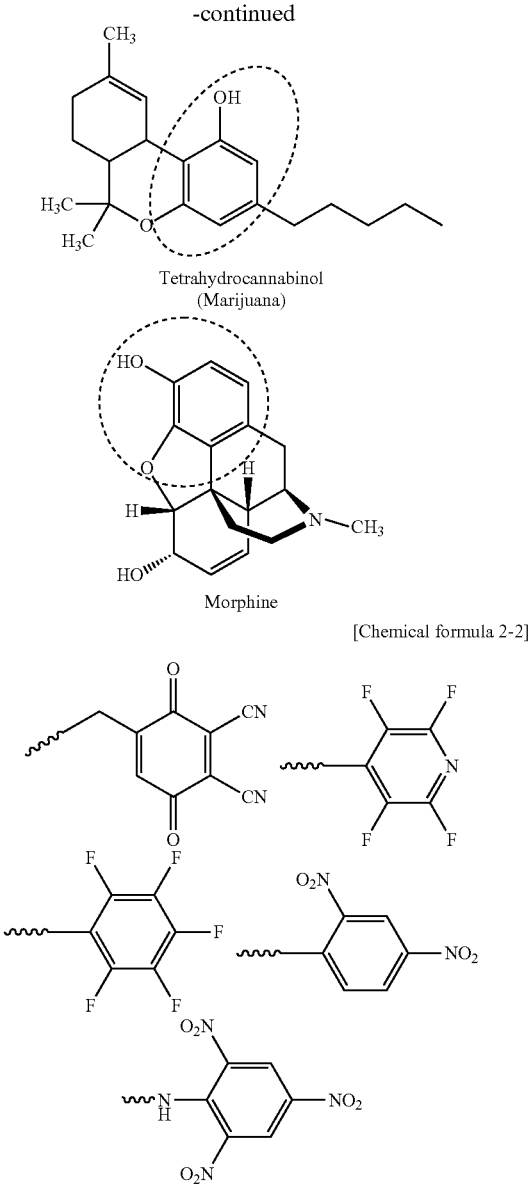

Tetrahydrocannabinol
(Marijuana)

Morphine

[Chemical formula 2-2]

Various known materials may be used as the materials containing the functional groups represented by the above chemical formulas 1-2 or 2-2.

According to example embodiments, the pre-concentrator including the three-dimensional nano structure may be easily provided in the trench of the base substrate.

Figure 10:
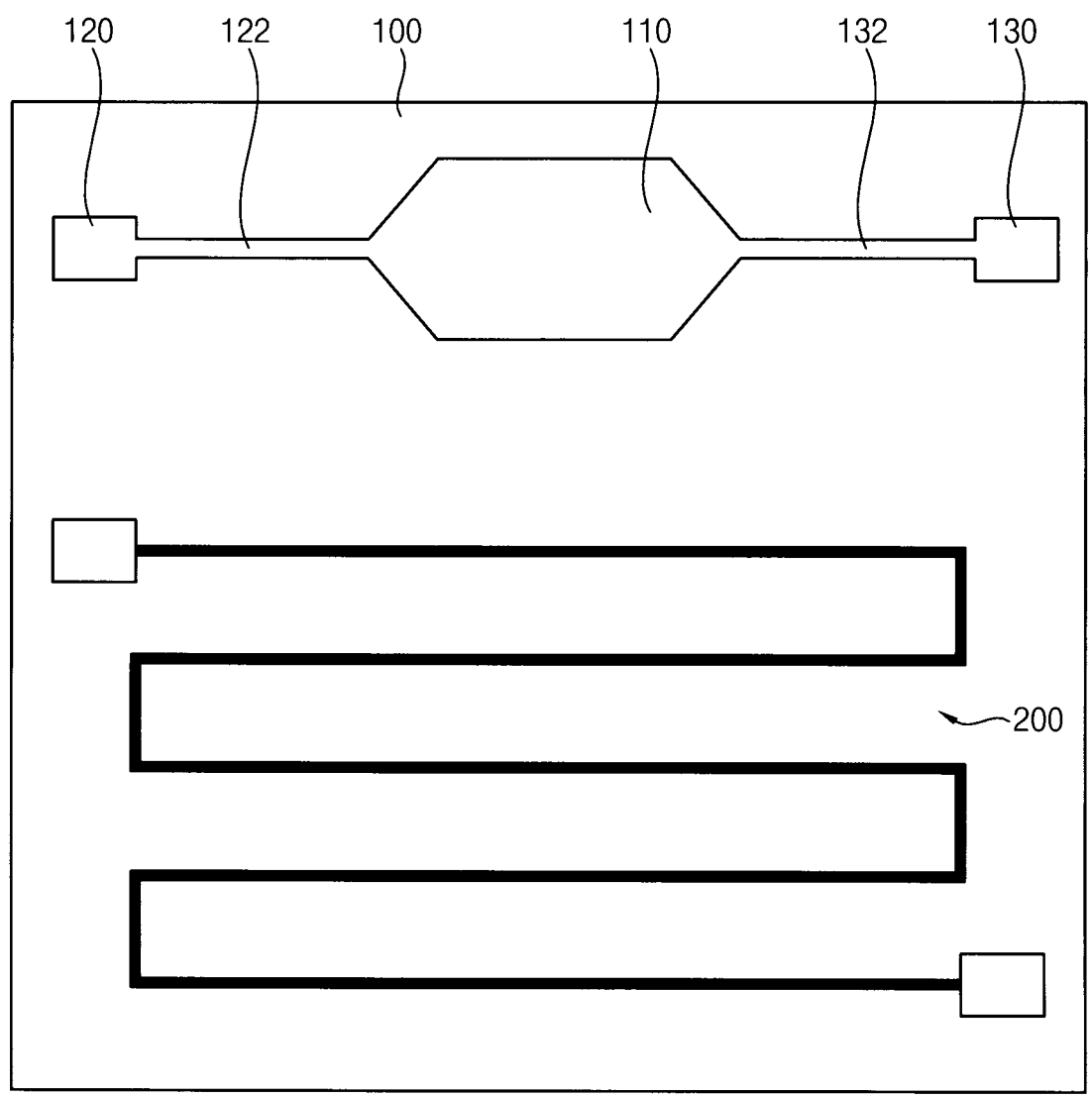
FIG. 10 is a plan view illustrating a pre-concentrator and a separator in accordance with an example embodiment of the invention.

FIG. 10 is a plan view illustrating a pre-concentrator and a separator in accordance with example embodiments of the invention.

In an example embodiment, the gas sample may be provided into the concentration section 110 through the injection section 120 and the injection channel 122. Further, the concentrated gas sample from the concentration section 110 may be discharged through the discharge channel 132 and the discharge section 130. The discharged gas sample may be provided into a separator 200 via a microfluid channel. Preferably, the separator 200 may be mounted or integrated on a substrate similar to the base substrate 100.

Figure 11:
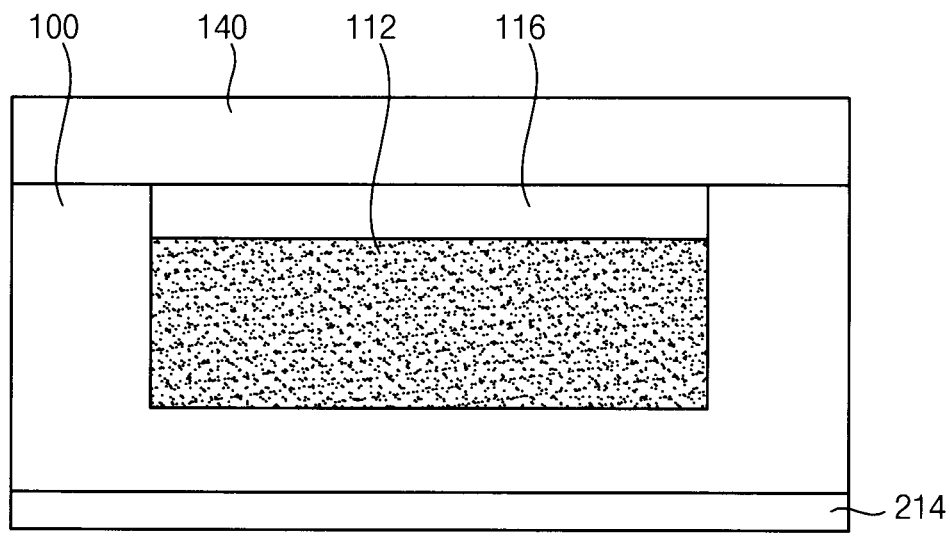
FIG. 11 is a cross sectional view illustrating a pre-concentrator in accordance with an example embodiment of the invention.

FIG. 11 is a cross sectional view illustrating a pre-concentrator in accordance with example embodiments of the invention.

Referring to FIG. 11, the pre-concentrator may include a base substrate 100 having a trench, a three-dimensional nano structure 112 disposed in the trench, a cover member 140 covering the trench and coupling to the base substrate 100, and a lower metal layer 214.

In an example embodiment, a metal layer may not be disposed between the three-dimensional nano structure 112 and the base substrate 100 such that the three-dimensional nano structure 112 may contact an inside of the base substrate 100. The lower metal layer 214 may be attached to a lower face of the base substrate 100, and may be used as a heating member for the three-dimensional nano structure 112 utilizing Joule heat.

As described above, the three-dimensional nano structure 112 may be obtained by an electroplating process as well as a chemical vapor deposition process, an atomic layer deposition process, an electroless plating process, a liquid metal infiltration process, etc.

The pre-concentrator according to example embodiments of the invention may be used for detecting volatile organic compounds, explosive compounds, etc.

Figure 12:
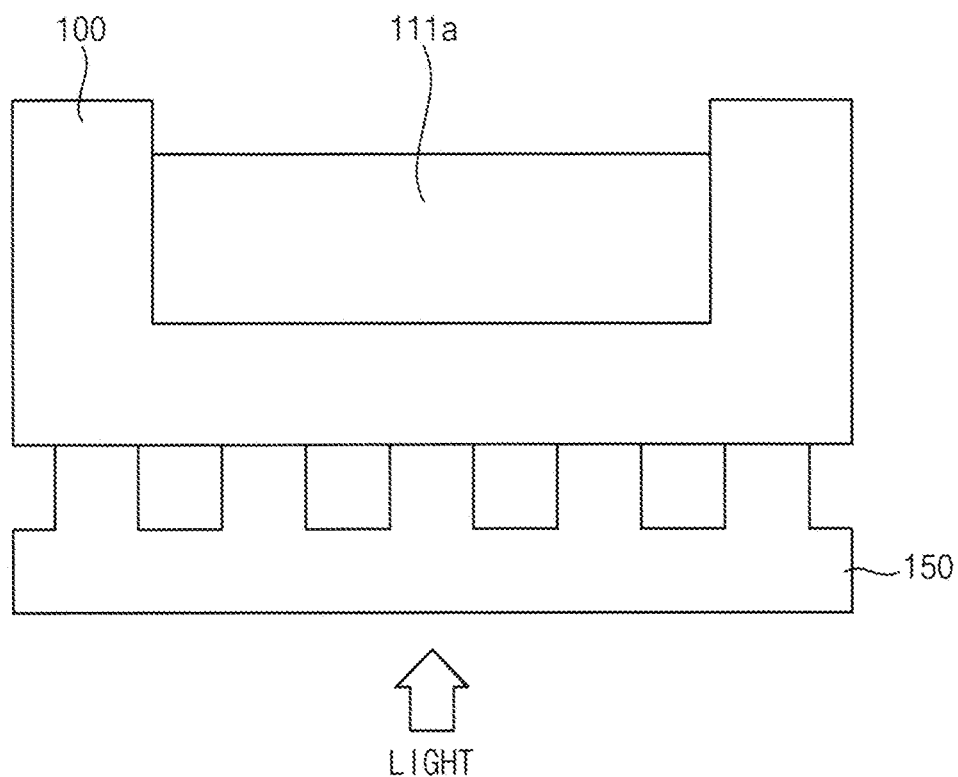
FIGS. 12 to 14 are cross sectional views illustrating a method of manufacturing a pre-concentrator in accordance with an example embodiment of the invention.
Figure 13:
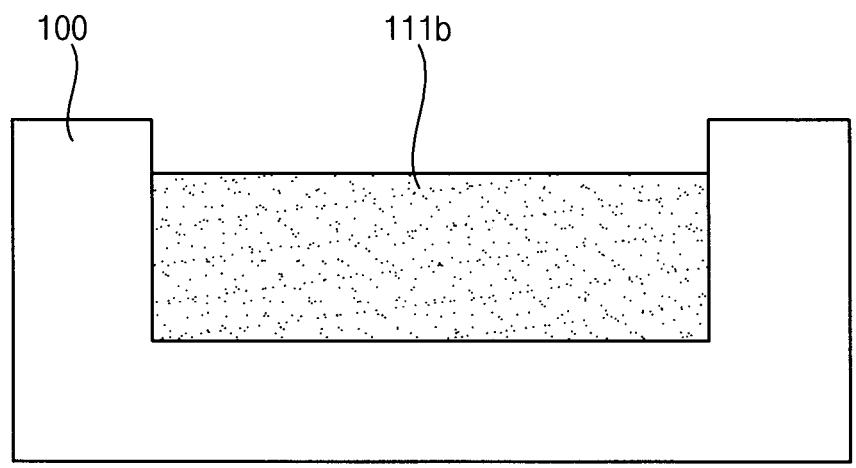
Figure 14:
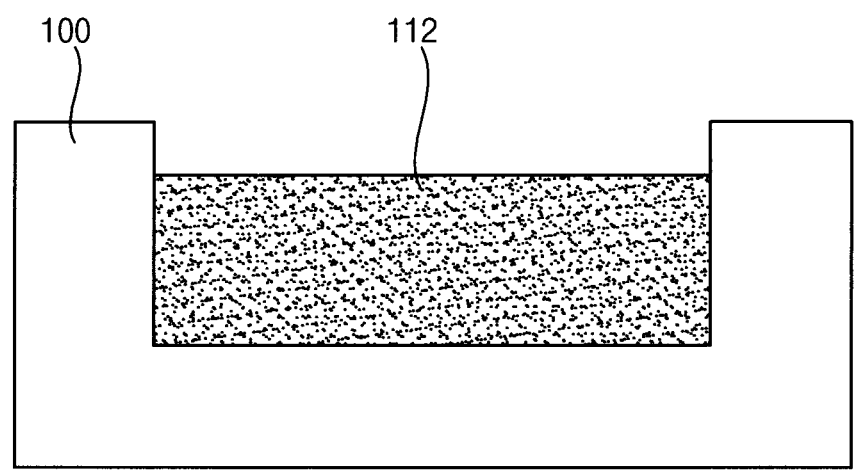

FIGS. 12 to 14 are cross sectional views illustrating a method of manufacturing a pre-concentrator in accordance with an example embodiment of the invention.

Referring to FIGS. 12 and 13, a photosensitive film 111a may be formed in a trench formed on an upper face of a base substrate 100. Then, a light having a three-dimensional distribution may be irradiated onto the photosensitive film 111a though a phase mask 150.

When the photosensitive film 111a includes a negative-tone photoresist, an unexposed portion thereof may be removed by a developing solution whereas an exposed portion thereof may remain. Therefore, a three-dimensional porous mold 111b having three-dimensional nano pores may be obtained.

In the above-described method, the base substrate 100 may serve as an optical medium between the phase mask 150 and the photosensitive film 111a so that the three-dimensional porous mold 111b having improved structural uniformity and reliability may be formed in the trench without the additional optical medium member illustrated in FIG. 6.

In an example embodiment, the base substrate 100 may include a material having high translucency and high refractive index, for example, glass, sapphire or quartz, and preferably may include glass such as soda lime glass.

Referring to FIG. 14, a three-dimensional nano structure 112 may be formed using the three-dimensional porous mold 111b.

Particularly, a reversed filling structure may be formed by filling at least a portion of the three-dimensional porous mold 111b. Then, the three-dimensional nano structure 112 corresponding to the reversed filling structure may be obtained by removing the three-dimensional porous mold 111b.

For example, the three-dimensional nano structure 112 may be formed by a chemical vapor deposition process, an atomic layer deposition process, an electroplating process, an electroless plating process, a liquid metal infiltration process, etc.

For example, the three-dimensional nano structure 112 may include various materials such as metals, ceramics, semiconductors, low molecular organic compounds, polymers, etc. For example, the three-dimensional nano structure 112 may include cerium oxide ($CeO_2$), aluminum oxide ($Al_2O_3$), titanium oxide ($TiO_2$), zirconium oxide ($ZrO_2$), zinc oxide (ZnO) and titanium nitride (TiN), or combinations thereof. In some example embodiments, the three-dimensional nano structure 112 may include gold, silver, platinum, palladium, ruthenium, rhodium, iridium, vanadium, nickel, cobalt, copper, tungsten, molybdenum, manganese, aluminum, iron, or combinations thereof. The materials for the three-dimensional nano structure 112 of the invention may not be limited to the above materials, and thus various materials may be used for the three-dimensional nano structure 112 depending on types of substances to be detected.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A method of manufacturing a pre-concentrator, which comprises:
    forming a three-dimensional porous mold in a trench of a base substrate;
    forming a reverse filled structure by filling pores of the three-dimensional porous mold; and
    forming a three-dimensional porous nano structure including arranged pores three-dimensionally connected to each other by removing the three-dimensional porous mold,
    wherein forming the three-dimensional porous mold comprises:
        forming a photosensitive film in the trench such that an upper surface of the photosensitive film is lower than an upper surface of the base substrate where the trench is not formed;
        coating a composition on the photosensitive film to fill the trench;
        curing the composition to form an optical medium member, wherein the optical medium member has a protrusion, which is disposed in the trench to contact the upper surface of the photosensitive film, the optical medium member further contacts the upper surface of the base substrate, and the optical medium member has a flat upper surface having a width larger than a width of the trench;
        disposing a phase mask having a concave and convex structure over the optical medium member such that the concave and convex structure contacts the flat upper surface of the optical medium member; and
        irradiating a light of a three-dimensional distribution onto the photosensitive film through the phase mask and the optical medium member.

2. The method of manufacturing a pre-concentrator of claim 1, wherein the phase mask and the optical medium member include a substantially same polymer.

3. The method of manufacturing a pre-concentrator of claim 2, wherein the phase mask and the optical medium member include at least one selected from the group consisting of PDMS (polydimetyl siloxane), PUA (polyurethane acrylate) and PEPE (perfluoropolyether).

4. The method of manufacturing a pre-concentrator of claim 1, wherein the three-dimensional nano structure includes at least one selected from the group consisting of cerium oxide ($CeO_2$), aluminum oxide ($Al_2O_3$), titanium oxide ($TiO_2$), zirconium oxide ($ZrO_2$), zinc oxide (ZnO) and titanium nitride (TiN).

5. The method of manufacturing a pre-concentrator of claim 1, wherein the three-dimensional nano structure includes at least one selected from the group consisting of gold, silver, platinum, palladium, ruthenium, rhodium, iridium, vanadium, nickel, cobalt, copper, tungsten, molybdenum, manganese, aluminum and iron.

* * * * *